(12) United States Patent
Caligor et al.

(10) Patent No.: US 8,768,036 B2
(45) Date of Patent: Jul. 1, 2014

(54) SYSTEM AND METHOD FOR DETECTING AND TRACKING CHANGE IN DENTAL X-RAYS AND DENTAL IMAGES

(75) Inventors: Dan Caligor, New York, NY (US); Ira Wallace, Narberth, PA (US)

(73) Assignee: EyeIC, Inc., Conshohocken, PA (US)

( * ) Notice: Subject to any disclaimer, the term of this patent is extended or adjusted under 35 U.S.C. 154(b) by 890 days.

(21) Appl. No.: 13/501,648

(22) PCT Filed: May 22, 2009

(86) PCT No.: PCT/US2009/044965
§ 371 (c)(1),
(2), (4) Date: Aug. 8, 2012

(87) PCT Pub. No.: WO2009/143417
PCT Pub. Date: Nov. 26, 2009

(65) Prior Publication Data
US 2013/0044932 A1    Feb. 21, 2013

Related U.S. Application Data

(60) Provisional application No. 61/055,759, filed on May 23, 2008.

(51) Int. Cl.
*G06K 9/00* (2006.01)
*A61C 3/00* (2006.01)

(52) U.S. Cl.
USPC .............................. 382/132; 382/219; 433/24

(58) Field of Classification Search
CPC .................................... G06K 9/00; A61C 3/00
USPC ......... 382/100, 103, 128–133, 154, 162, 168, 382/173, 181, 189–193, 209, 219, 232, 254, 382/274, 276, 285–294, 305, 312; 378/4, 378/21, 38; 433/24, 215
See application file for complete search history.

(56) References Cited

U.S. PATENT DOCUMENTS

| | | | |
|---|---|---|---|
| 6,868,172 B2 * | 3/2005 | Boland et al. | 382/132 |
| 2005/0089822 A1 * | 4/2005 | Geng | 433/215 |
| 2006/0285636 A1 * | 12/2006 | Razzano | 378/38 |
| 2007/0207437 A1 * | 9/2007 | Sachdeva et al. | 433/24 |
| 2008/0273779 A1 * | 11/2008 | Pekar | 382/131 |

* cited by examiner

*Primary Examiner* — Seyed Azarian
(74) *Attorney, Agent, or Firm* — Baker & Hostetler LLP (57) ABSTRACT

A system and method for detecting and/or rendering easily visible changes in dental images over time so as to identify bone loss, tooth movement, and other forms of change that uses dental images with similar perspectives but taken at different points in time and adjusts one or both of the dental images so as to compensate for differences in perspective, size, and rotation to thereby register the digital images to each other.

24 Claims, 7 Drawing Sheets

SYSTEM AND METHOD FOR DETECTING AND TRACKING CHANGE IN DENTAL X-RAYS AND DENTAL IMAGES

CROSS-REFERENCE TO RELATED APPLICATIONS

This application is the National Stage of International Application No. PCT/US2009/044965, filed May 22, 2009, which claims the benefit of U.S. Provisional Application No. 61/055,759, filed May 23, 2008, the disclosures of which are incorporated herein by reference in their entireties.

FIELD OF THE INVENTION

The invention relates to a system and method for detecting and tracking changes in dental x-rays and, more particularly, to a method for any of: (1) detecting bone loss in a patient's jaw, (2) monitoring change and rate of change resulting from normal growth in children and adolescents, (3) tracking and documenting change resulting from the application of braces or other orthodonture, and (4) other forms of change detection and change monitoring. In an alternate embodiment, the invention can be used to overlay two images of differing types (e.g., x-ray and photo).

BACKGROUND OF THE INVENTION

Detecting and tracking change has several important applications in dentistry. These include monitoring for bone loss in the jaw, monitoring adolescents for the cessation of growth (a pre-requisite for some procedures), and patient education in several fields including orthodontics.

Loss of bone density in the upper and lower jaws is a common occurrence in a wide range of dental patients and can cause severe problems ranging from tooth loss to infection. Causes for bone loss include extracted teeth, poor or misaligned bridge work, trauma and naturally occurring misalignment as well as other factors that prevent the root structures connecting teeth to jaw from being properly stimulated.

Bone loss becomes more likely as a patient ages and is extremely common, especially in specific patient groups. It is also is an early indicator of osteoporosis, a condition which afflicts a large portion of the population, especially older women, and thus has relevance beyond the direct implications for dental health. Finally, the onset of bone loss can be quite sudden in some circumstances, progressing rapidly in a matter of months. The condition can be checked if identified, but cannot be reversed. Left unchecked, the consequences are extreme. These considerations, combined with the prevalence of the condition, make monitoring all adults for dental bone loss an important preventive measure. If identified early, a number of measures can be taken to slow or stop bone loss, as well as to repair damage and related conditions before they can spread or worsen.

In general, patients experiencing bone loss are not aware of the condition until they are informed of it by their dentist. Generally this happens only after the bone loss has progressed significantly. Bone loss can also begin and progress rapidly, making this general lack of awareness all the more problematic.

A number of technologies exist for monitoring patients for jaw bone loss. For example, MRI and CT scans are sometimes used to assess bone loss. However, these procedures rely on large, expensive and specialized devices and are not practical in most dental office settings. For these and other reasons, common practices generally rely on far simpler techniques, specifically periodontal probing or manual (unassisted) comparison of x-rays.

By way of summary, common methods for identifying bone loss in patients include:
1. Periodontal probing—measuring of the depth of pockets around the teeth with a small probe marked off like a ruler;
2. Examining dental x-rays, either singly or in side-by-side manual comparison with similar x-rays; and
3. Assorted approaches relying on specialized equipment or procedures, including:
    a. MRI (Magnetic Resonance Imaging);
    b. CT (Computerized Tomography) Scan; and
    c. Biopsy (to assess bone density).

Each of these methods has a number of short-comings, however. For example, using probes requires careful and systematic checking across the mouth at regular intervals, and can be both time consuming and unreliable. It is also imprecise, and does not lend itself to documentation or tracking X-rays are often difficult to compare due to differences between images arising from parallax, image rotation, image framing or other factors. Tracking changes in jaw bone volume or density using x-ray comparison is time-consuming and error-prone, especially if differences arising from how the images are captured introduce subtle differences not attributable to bone loss. Finally, neither periodontal probing nor x-ray comparison is effective in patient education, as probes provide little in the way of visual aids, and x-rays can be difficult for lay people to understand and even more so to compare. Patient education is an important consideration, as the effects of bone loss are often not evident to the patient, and motivating patients to change behaviors immediately is important in heading off progression.

New techniques are desired that address the problems described above by allowing dentists to identify, assess and monitor bone loss and other forms of change over time using historical or new dental x-rays as a baseline in a cost-effective manner, or which allow dentists to educate patients by creating visual aids. The present invention addresses these needs in the art.

SUMMARY OF THE INVENTION

The Dental Flicker (DF) technique is designed to address the problems described above by allowing dentists to identify, assess and monitor change over time using historical or new dental x-rays as a baseline. The process makes it easier to identify and to present for examination relatively small quantities of change which might in other circumstances go unnoticed or unremarked. As a result, bone loss can be identified and addressed before the condition can progress, leading to earlier and more effective treatment. Similarly, the advent or cessation of change can be more easily and accurately identified, with numerous applications. Additional benefits of the DF technique include (1) enabling the rapid and automated creation of documentation, (2) providing a foundation for quantitative measurement and tracking of bone loss, and (3) greatly enhanced patient education. The DF technique is a software-based solution and requires no additional hardware beyond what virtually all dental practices already possess (specifically, a digital x-ray and/or photographic capture device—or an analog capture device and a scanner—and at least one computer having a processor, a display and memory sufficient to store and implement software embodying the methodology described herein).

The DF technique can be employed with a variety of x-ray types captured in a variety of contexts. The DF technique can also be used with dental photographs. The DF technique also can be used on two or more images taken over varying intervals of time. Beyond its application to identifying, presenting for examination, and tracking bone loss, the DF technique can also be used to identify, present for examination, and monitor other conditions where tracking change over time is an important consideration. Examples include monitoring growth in children and adolescents, monitoring conditions such as tooth erosion, and charting the changes produced by orthodontic procedures.

The Dental Flicker technique described herein can be applied in at least two ways: (1) using computer-aided registration and alignment to create a "flicker," and (2) using techniques such as Cross-Image Mapping (e.g., described in U.S. Provisional Patent Application No. 61/049,954, filed May 2, 2008, entitled: "Cross-Image Mapping (CIM): A System and Method for Using Image Alignment to Create and/or Map Annotations Across Disparate Images") or similar or comparable techniques to apply "before and after" indicators to a single image.

A first Dental Flicker embodiment uses computer-aided registration and alignment to create a "flicker" by establishing a baseline using an historical (existing) x-ray or by creating a new one, by capturing a new x-ray of the same area captured from a similar perspective, and using a DF application to create a "flicker" by modifying one more of the source images to enable or improve direct comparison using computer software, and/or overlaying the resulting registered images in a "flicker" display, whereby two or more aligned images are presented in the same view on an alternating basis as a "movie." The method may also include the optional step of employing one or more of the following CIM or comparable techniques to present for examination, quantify and/or document changes:

1. Applying CIM or comparable techniques to mark "before and after" locations of bone edge or other landmark at different times and display on one or more source or aligned images or on flicker; and/or
2. Applying additional CIM or comparable techniques to quantify the movement or loss of bone in absolute units (e.g., mm) or relative change (e.g., percentage loss)

A second Dental Flicker embodiment uses CIM (Cross-Image Mapping) or comparable techniques to apply "before and after" indicators to a single image. This method includes the steps of mapping two or more images using manual or automated registration, using a CIM module to create formulae for mapping landmarks in any given image to the corresponding point in any other source (unmodified) or aligned or mapped (modified per method 1 above) images, and the user marking "before and after" locations of bone edge or other landmark in two or more images. These marks are then mapped across images using the formulae and can be presented on a single image indicating the relative positions of the landmark over time. Optionally, as with the first embodiment described above, additional CIM or comparable techniques may be applied to quantify the movement or loss of bone in absolute units (e.g., mm) or relative change (e.g., percentage loss).

More than two points in time can be compared using the technique of either embodiment above by repeating the above steps and adding the resulting increment of change to the previously documented ones. In this way, a flicker or CIM-based comparison can document many increments of change over an extended period of time.

In another embodiment of Dental Flicker, photographs and x-rays can be aligned and overlaid allowing dentists and patients to see, for example, the relationship between specific locations on the gum and the teeth or bones beneath the gum. This can be helpful in several ways, for instance allowing dentists and patients to see the relationship between specific spots or conditions of the gum and features which are not normally visible (such as those that can be seen in an x-ray).

Beyond its application to identifying, presenting for examination, and tracking bone loss, the Dental Flicker technique can also be used to identify, present for examination, and monitor other conditions where tracking change over time is an important consideration. Examples include tracking the progression of tooth erosion and monitoring the shifting of teeth.

The DF technique also has applications in several specialties where monitoring and documenting change is important or useful. These include (1) monitoring adolescent patients needing implants and certain other surgeries which cannot be undertaken until growth of the jaw and related areas has stopped and (2) tracking and documenting shift over time of patients treated with various orthodontic procedures and appliances. While some of these applications apply to critical health-related areas, all offer opportunities to educate patients by illustrating change in easy to perceive and easy to understand ways. It is anticipated that additional applications of the DF technology will emerge for specific uses. Examples include tracking and demonstrating tooth erosion and preparing "before and after" comparisons for cosmetic procedures.

Finally, Dental Flickers can be created which combine x-rays and other types of image of the same area captured during the same or different periods of time. For instance, photographs of teeth and gums can be flickered with x-ray images to show the relationship between, for example, condition of gums and condition of teeth and bones beneath that portion of the gums

DETAILED DESCRIPTION OF ILLUSTRATIVE EMBODIMENTS

A detailed description of illustrative embodiments of the present invention will now be described with reference to FIGS. 1-7. Although this description provides a detailed example of possible implementations of the present invention, it should be noted that these details are intended to be exemplary and in no way delimit the scope of the invention.

First Embodiment

Figure 1:
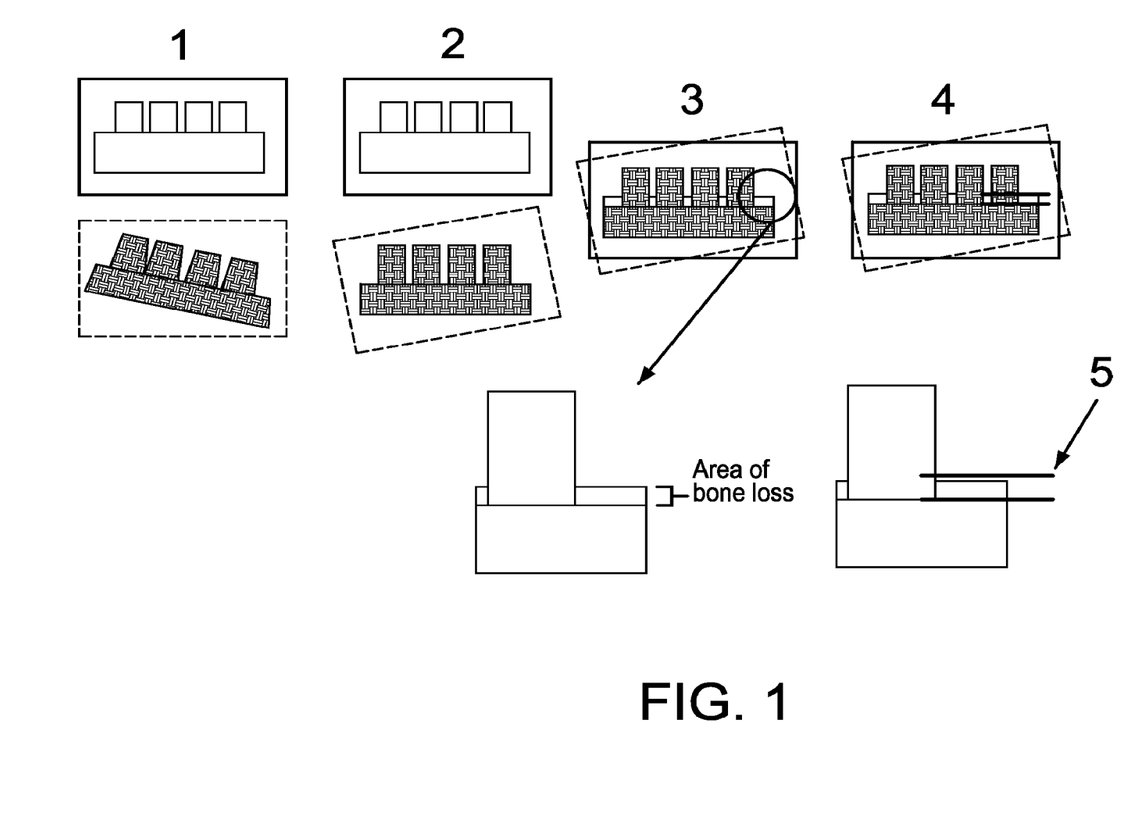
FIG. 1 illustrates the alignment of dental images in accordance with the first embodiment of the invention where image A is taken straight on and image B is from a slightly lower perspective of the jaw with a slight rotation.

In accordance with a first embodiment of the invention, computer-aided registration and alignment is used to create a "flicker." Such a method in accordance with the first embodiment includes establishing a baseline using a historical (existing) x-ray or by creating a new one. Virtually any x-ray (including those from digital sources as well as analog sources which have been scanned) can serve as a baseline, as long as it shows the features or landmarks to be examined, and the perspective, image type and rough image attributes can be approximated in subsequently prepared images. FIG. 1 shows two x-rays of the same area captured from a similar perspective. As illustrated at (1), two source images of the patient from a similar perspective are taken at different points in time, where, in this case, the first image A is taken straight on the tooth and the second image B is taken from a slightly lower perspective of the jaw, with a slight rotation. The technique is most effective when these images are close approximations of the baseline in terms of perspective, magnification, image type and so on. Depending on the specifics, however, the technique can tolerate significant differences in these attributes.

A DF application is then used to create a "flicker" in a two-step process. In the first step, one or more of the source images is modified as illustrated at (2) in FIG. 1 to compensate for differences in perspective, rotation, and the like between the images A and B, for example, to thereby enable or improve direct comparison using computer software. These modifications may include registering, warping, rotating or otherwise changing the orientation and shape of the image and/or its contents. Methods for aligning images include automated registration and alignment algorithms and manual registration techniques, as described below. In some cases, the changes to bone mass or other factors (such as damaged or missing teeth) may render the two images difficult or impossible to align if the process is based on their entire contents. In these cases, it may be necessary for the user to identify the portion of one or both images (e.g., a specific tooth or area) upon which to base the alignment. The modifications derived from these two areas can then be generalized and applied to the remainder of the images (i.e., the portions excluded from the area on which alignment was based). Furthermore, in some cases (such as when the relative position of upper and lower jaws differs between images), relative positioning of areas of the two images may be different for reasons other than change, rendering the images difficult to align and/or the resulting flicker difficult to interpret. These cases may require that the images be broken into portions, these portions aligned individually, and the resulting aligned portions reassembled with the relative position of these areas adjusted in one or both images to facilitate flickering. In other cases, precise alignment will be difficult or impossible to achieve. In these cases, a best-fit approach can be employed to achieve substantially the same results.

In the second step of the step of creating a "flicker," the resulting aligned images are overlaid in a "flicker" display as shown at (3) in FIG. 1, whereby two or more aligned images are presented in the same view on an alternating basis as a "movie." In this flicker presentation of closely aligned images, all objects that have not moved or changed will appear stationary, while change of any sort will appear as motion. If images are imperfectly aligned, shift in jaw bone relative to other landmarks will still be evident to both educated and lay observers. As illustrated in FIG. 1, the differences between the images will reflect the bone loss (or other change) over the time between the images.

Optionally, as illustrated at (4) in FIG. 1, the first embodiment may also optionally employ one or more of the following CIM or comparable techniques to present, quantify and/or document changes:

1. Apply CIM or comparable techniques to mark "before and after" locations of bone edge or other landmark at different times. These can be displayed on the flicker, the aligned images, or the source images; and/or 2. Apply additional CIM or comparable techniques to quantify the movement or loss of bone in absolute units (e.g., mm) or relative change (e.g., percentage loss).

The bone loss in this case will be represented at (5) by user or computer generated "before and after" drawings as illustrated. It is noted that more than two points in time can be compared using either technique (1) or (2) by repeating the above steps and adding the resulting increment of change to the previously documented ones. In this way, a flicker or CIM-based comparison can document many increments of change over an extended period of time.

Figure 2:
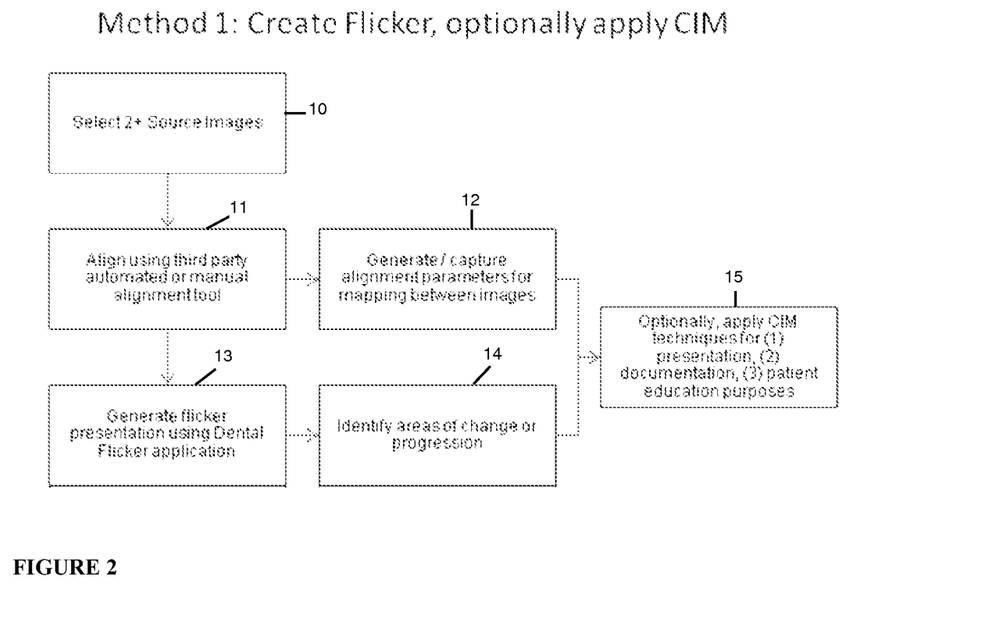
FIG. 2 illustrates the implementation of the first embodiment of the invention in software.
Figure 3:
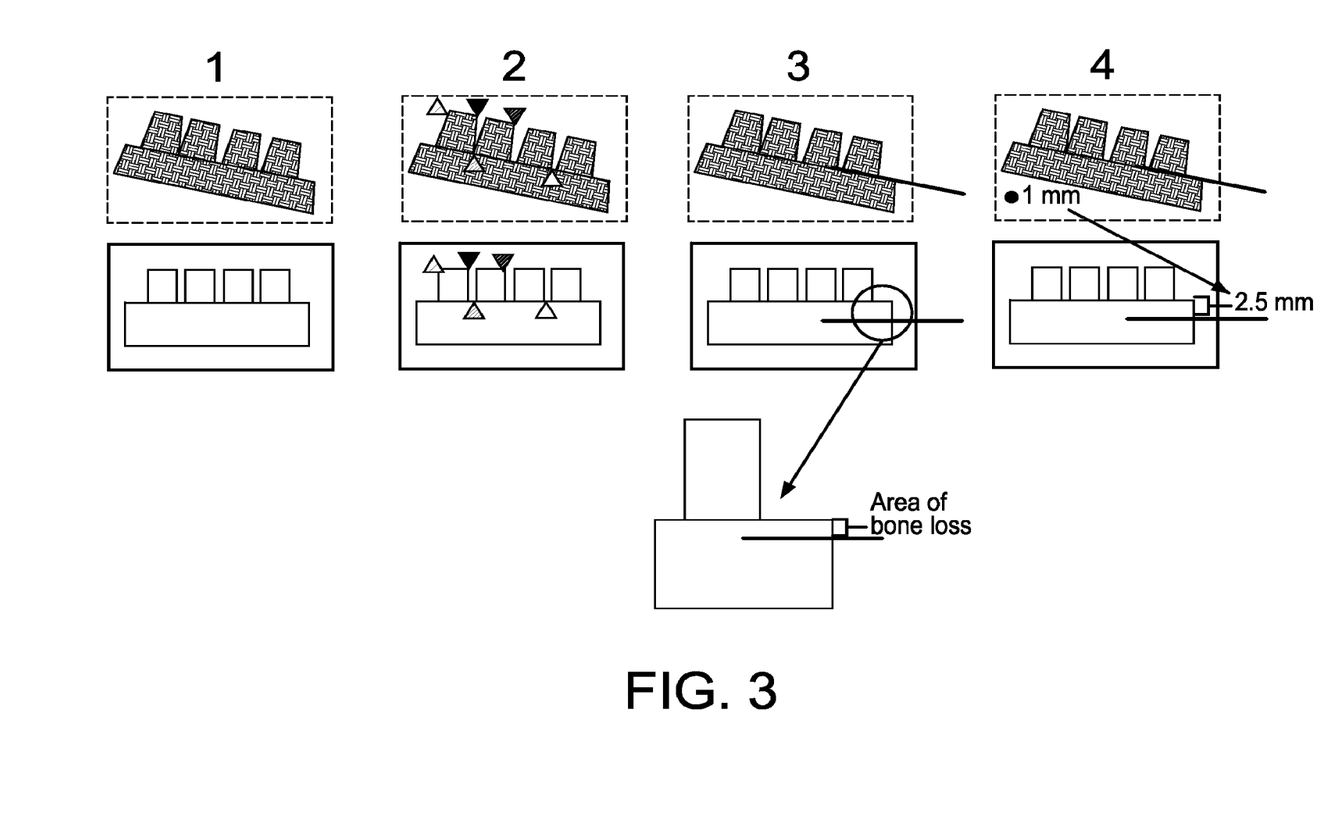
FIG. 3 illustrates the alignment of dental images in accordance with the second embodiment of the invention where image A is taken straight on an image B is from a slightly lower perspective of the jaw with a slight rotation.

FIG. 2 illustrates the flow of software for implementing the first embodiment of the invention as software on a computer at, for example, a dentist's office. As illustrated, the process starts at 10 by selecting two or more source images for comparison (A and B in the above example) and then aligning the images at 11 using an automated or manual alignment tool. Alignment parameters for mapping between images may be generated or captured at 12. A flicker presentation is then generated at 13 using the dental flicker application described herein and areas of change or progression within the images are identified at 14. CIM or comparable techniques are optionally applied to the resulting images for presentation, documentation, and/or patient educational purposes at 15.

Second Embodiment

In accordance with a second embodiment of the invention, Cross-Image Mapping (CIM) or comparable techniques are used to apply "before and after" indicators to a single image. Such a method in accordance with the second embodiment allows a DF software user (e.g., a doctor, nurse or technician) to map two or more images using manual or automated registration. These aligned images do not need to be displayed for this technique to be effective, so actual modifications to the image are necessary only if called for by the mapping approach employed. As in the first embodiment, the first step includes acquiring two images of the patient from similar perspectives taken at two different points in time. As illustrated at (1) in FIG. 3, image A is taken straight on and image B is taken from a slightly lower perspective of the jaw with a slight rotation. The images are manually registered by the user as illustrated at (2) in FIG. 3. The CIM module of the DF application then creates formulae for mapping landmarks in any given image to the corresponding point in any other source (unmodified) or aligned or mapped (modified per step 1 above) images. For example, the CIM mapping parameters may include the degrees of rotation to align the images, the units of top edge expansion, the units of additional height for each 100 pixels from the bottom of the image (the top is stretched the most), and the units for shifting the image center left and up in the x and y directions, respectively. However, methods other than CIM may provide for such mark-ups and may be used as appropriate.

Next, the user marks "before and after" locations of bone edge or other landmark in two or more images. These marks are then mapped across images by the CIM software using the formulae from the previous step, and can be presented on a single image as shown at (3) in FIG. 3, indicating the relative positions of the landmark over time. Optionally, as in the first embodiment described above, additional CIM or comparable techniques may be applied to quantify the movement or loss of bone in absolute units (e.g., mm) or relative change (e.g., percentage loss) as illustrated at (4) in FIG. 3. As in the first embodiment, more than two points in time can be compared by repeating the above steps and adding the resulting increment of change to the previously documented ones. In this way, a flicker or CIM-based comparison can document many increments of change over an extended period of time.

Figure 4:
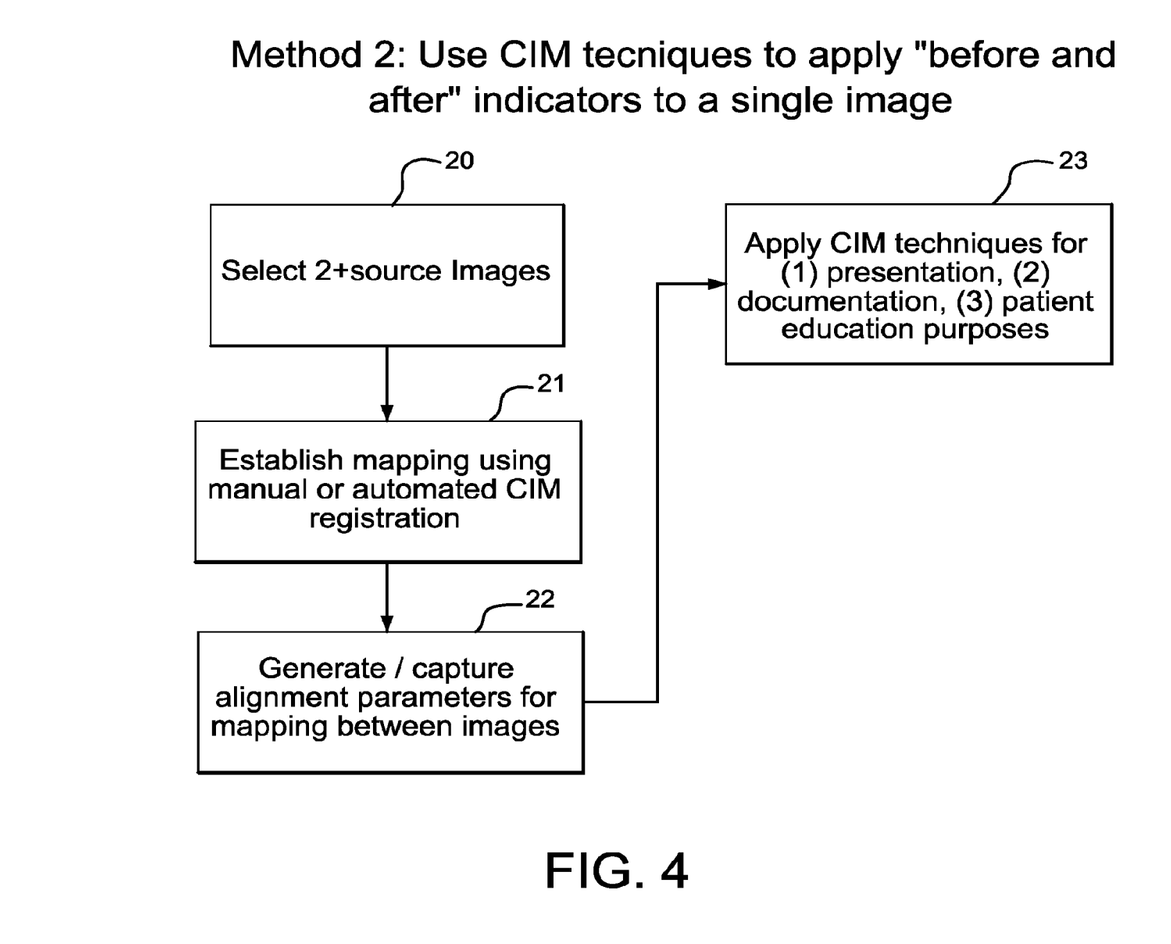
FIG. 4 illustrates the implementation of the second embodiment of the invention in software.

FIG. 4 illustrates the flow of software for implementing the second embodiment of the invention as software on a computer at, for example, a dentist's office. As illustrated, the process starts at 20 by selecting two or more source images for comparison (A and B in the above example) and then establishing mapping at 21 using manual or automated registration as defined above. Alignment parameters for mapping between images may be generated or captured at 22. CIM or comparable techniques are optionally applied to the resulting images at 23 for presentation, documentation, and/or patient educational purposes. These techniques may include various forms of input, including mouse or other input device or selection of areas of an image based on density, color or other criteria, and may include various forms of presentation, including on-screen or hard-copy.

Third Embodiment

In accordance with a third embodiment of Dental Flicker techniques, images of different types (for example photos and x-rays) but sharing certain landmarks (for example, teeth) in common, are aligned and/or mapped to allow location of a specific spot in one image on another. For example, this embodiment might be used to allow dentists and patients to relate a specific spot on the gums to the bones and/or teeth below that spot on the gums.

Figure 5:
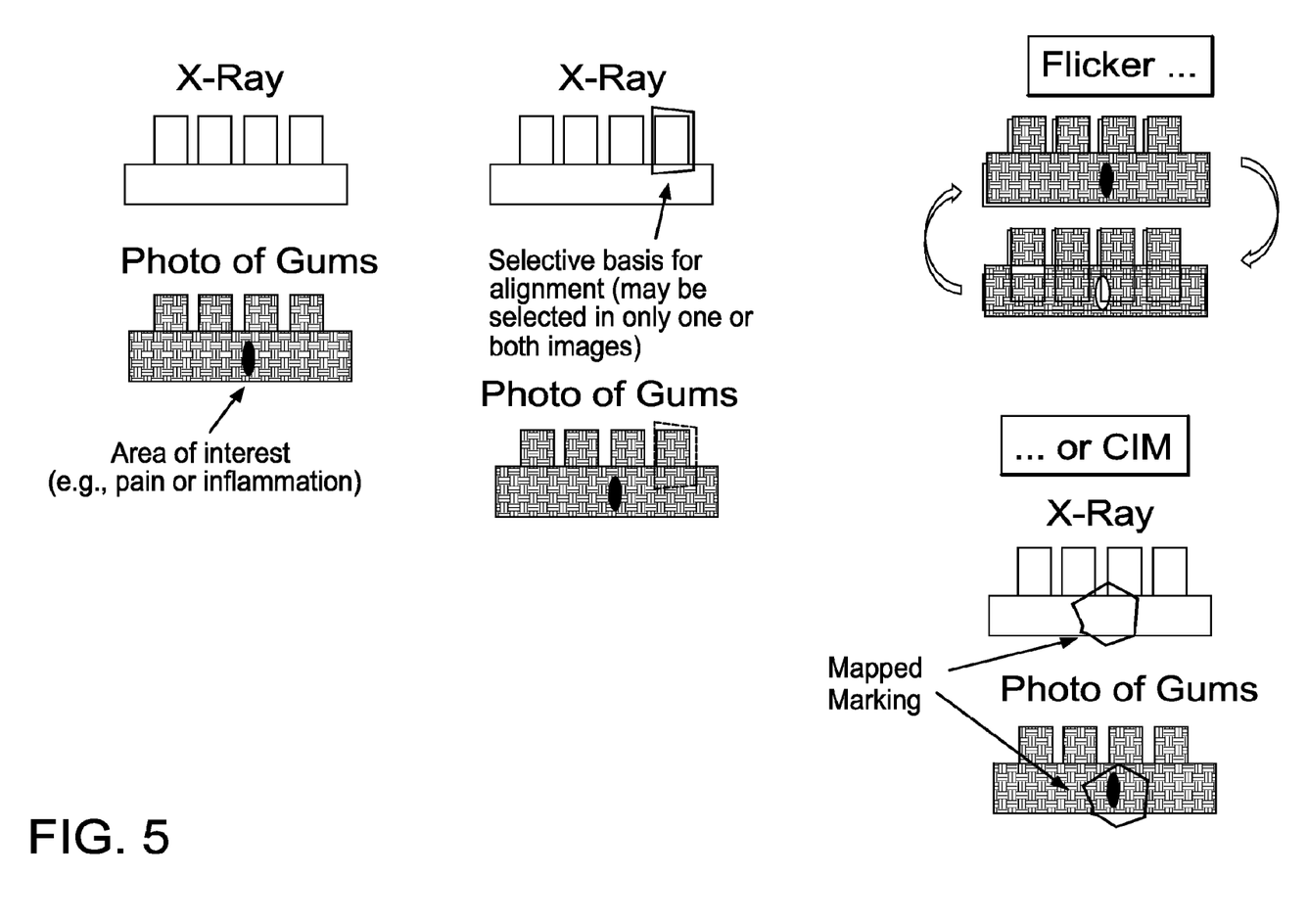
FIG. 5 illustrates the flickering of two image types, in this case an x-ray and a photograph of the same areas.

In such cases it may be necessary to align the images using only selected portions of one or both unaligned (source) images. FIG. 5 illustrates the flickering of two image types, in this case an x-ray and a photograph of the same areas. As illustrated in FIG. 5, the user circles or otherwise identifies the common landmarks (e.g., visible portion of teeth). The system would then align the entire area of the images using only the identified portions as the basis of this alignment. It is noted that the area can be designated in one image (and the entire image aligned with the second using only the selection from the first image and the entire second image) as the basis of alignment, or an area can be designated in both images. Those skilled in the art will appreciate that in this embodiment the images will generally be generated at about the same time, though not always.

Independent Alignment of Portions of Images

Figure 6:
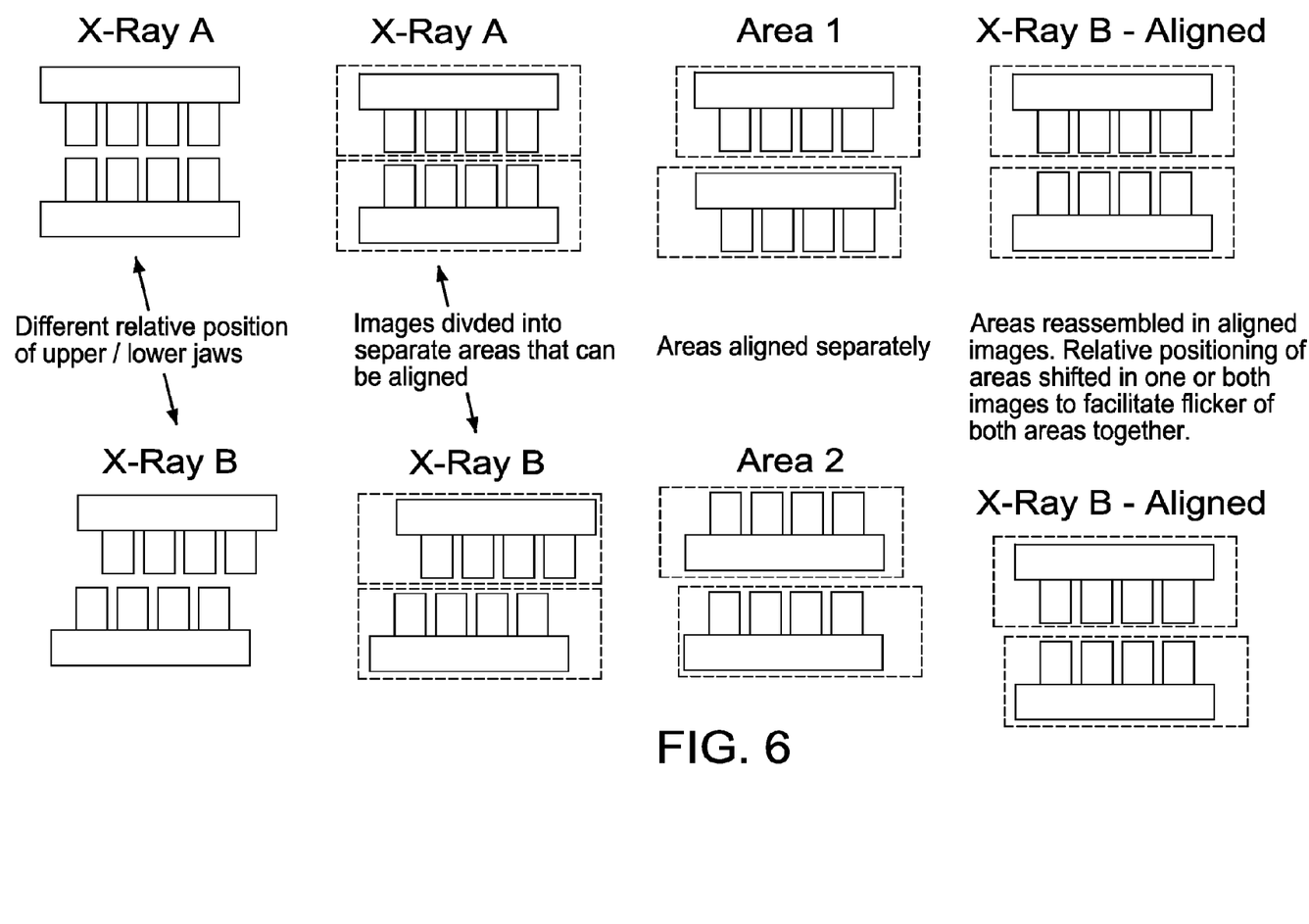
FIG. 6 illustrates breaking an image including two or more areas for alignment (e.g., the top and bottom of the patient's jaw.) into two or more areas for independent alignment.

In any of the embodiments above, it may be desirable to break each image into two or more areas for alignment, as when comparing dental x-rays of the top and bottom of the patient's jaw. As illustrated in FIG. 6, each image is broken into two or more areas, each pair (area 1 in image A and area 1 in image B, area 2 in image A and area 2 in image B, and so on) are aligned independently. The resulting aligned areas are then reassembled, with the relative positioning of areas 1, 2, etc. in one or more images changed so they will align when flickered.

Figure 7:
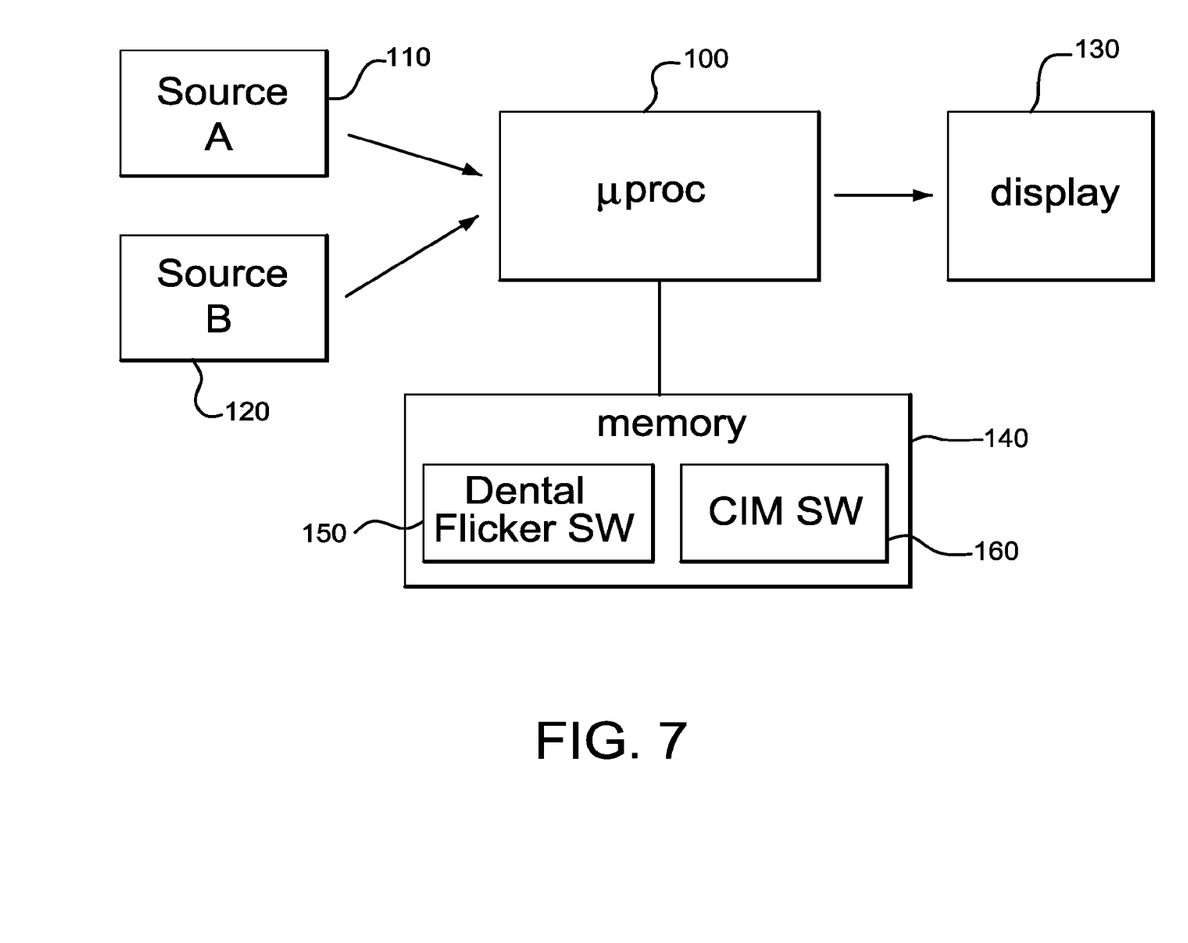
FIG. 7 illustrates an exemplary computer system for implementing the "dental flicker" technique of the invention.

FIG. 7 illustrates an exemplary computer system for implementing the "dental flicker" technique of the invention. As shown, a microprocessor 100 receives two or more user-selected source images 110 and 120 and processes these images for display on display 130. Memory 140 stores software including the Dental Flicker algorithm 150 that is processed by microprocessor 100 for use in aligning the images and to generate and capture alignment parameters as described in connection with both embodiments above. CIM software 160 in accordance with the invention is also stored in memory 140 for processing by microprocessor 100.

Those skilled in the art also will readily appreciate that many additional modifications are possible in the exemplary embodiments without materially departing from the novel teachings and advantages of the invention. For example, those skilled in the art will appreciate that the methods of the invention may be implemented in software instructions that are stored on a computer readable medium for implementation in a processor when the instructions are read by the processor. The methods of the invention may also be implemented in a computer system including a processor, a display and sufficient memory for implementing software embodying the methods of the invention. Accordingly, any such modifications are intended to be included within the scope of this invention as defined by the following exemplary claims.

What is claimed:

1. A computer-implemented method for identifying and/or presenting changes in dental images over time, comprising the steps of:
    a user selecting using the computer a first dental image of a dental region taken at a first point in time and a second dental image of said dental region taken at a second point in time, wherein said second dental image is captured from a similar perspective as said first dental image;
    adjusting using the computer at least one of said first and second dental images so as to compensate for differences in perspective, size, and rotation to thereby register the first and second digital images to each other by creating formulae for mapping relative positions of landmarks between said first and second dental images and identifying corresponding points between the first and second dental images using said formulae; and
    the computer presenting the registered images in alternating views by overlaying the aligned first and second dental images over each other for display whereby differences between the first and second dental images are displayed in flicker as the registered images alternate views on the display.

2. A method as in claim 1, comprising the further steps of marking locations of a landmark in each of said first and second dental images and displaying any differences in location of said landmark between said first and second dental images.

3. A method as in claim 1, comprising the further steps of quantifying movement, change or loss of bone between said first and second dental images in absolute units or as a relative change there between.

4. A method as in claim 1, wherein said presenting step comprises the step of marking an area of interest on the first dental image and applying said formulae to identify the location of the area of interest on the second dental image.

5. A method as in claim 1, comprising the further steps of quantifying movement or loss of bone between said first and second dental images in absolute units or as a relative change there between.

6. A method as in claim 1, comprising the further steps of selecting a third dental image taken at a third point in time and repeating said adjusting and identifying steps for said third dental image with respect to said first and/or second dental images so as to document increments of change amongst said first, second and third dental images over said first, second and third points in time.

7. A method as in claim 1, comprising the further step of isolating areas of two images that have moved relative to each other, aligning these areas in the two images independently, and reassembling the areas with the aligned areas repositioned in one or both images to facilitate presentation in the alternating views.

8. A method as in claim 1, comprising the further step of selecting an area of one or both images upon which to base the adjustment and using only these areas to generate an adjustment that is applied to both images.

9. A computer system adapted to identifying and/or present changes in dental images over time, comprising:
   a processor;
   an output device; and
   a memory that stores instructions for processing by said processor, said instructions when processed by said processor causing said processor to:
   select a first dental image of a dental region taken at a first point in time and a second dental image of said dental region taken at a second point in time, wherein said second dental image is captured from a similar perspective as said first dental image;
   identify corresponding points between the first and second dental images using formulae for mapping relative positions of landmarks between said first and second dental images;
   adjust at least one of said first and second dental images so as to compensate for differences in perspective, size, and rotation to thereby register the first and second digital images to each other; and
   present the registered images in alternating views by overlaying the aligned first and second dental images over each other for display whereby differences between the first and second dental images are displayed in flicker as the registered images alternate views on said display.

10. A system as in claim 9, wherein said processor further marks locations of a landmark in each of said first and second dental images and displays any differences in location of said landmark between said first and second dental images on said display.

11. A system as in claim 9, wherein said processor further quantifies movement, change or loss of bone between said first and second dental images in absolute units or as a relative change there between.

12. A system as in claim 9, wherein said processor presents said differences between the first and second dental images by marking an area of interest on the first dental image and applying said formulae to identify the location of the area of interest on the second dental image.

13. A system as in claim 9, wherein said processor further quantifies movement or loss of bone between said first and second dental images in absolute units or as a relative change there between.

14. A system as in claim 9, wherein said processor further selects a third dental image taken at a third point in time and repeats said adjusting and identifying steps for said third dental image with respect to said first and/or second dental images so as to document increments of change amongst said first, second and third dental images over said first, second and third points in time.

15. A system as in claim 9, wherein said processor further isolates areas of two images that have moved relative to each other, aligns these areas in the two images independently, and reassembles the areas with the aligned areas repositioned in one or both images to facilitate presentation in the alternating views.

16. A system as in claim 9, wherein said processor further selects an area of one or both images upon which to base the adjustment and uses only these areas to generate an adjustment that is applied to both images.

17. A computer readable storage medium including instructions stored thereon that when processed by a processor causes said processor to identify and/or present changes in dental images over time, said instructions comprising instructions that cause said processor to perform the steps of:
   selecting a first dental image of a dental region taken at a first point in time and a second dental image of said dental region taken at a second point in time, wherein said second dental image is captured from a similar perspective as said first dental image;
   adjusting at least one of said first and second dental images so as to compensate for differences in perspective, size, and rotation to thereby register the first and second digital images to each other by creating formulae for mapping relative positions of landmarks between said first and second dental images and using said formulae to identify corresponding points between the first and second dental images; and
   presenting the registered images in alternating views by overlaying the aligned first and second dental images over each other for display whereby differences between the first and second dental images are displayed in flicker as the registered images alternate views on the display.

18. A computer readable storage medium as in claim 17, comprising instructions for implementing the further steps of marking locations of a landmark in each of said first and second dental images and displaying any differences in location of said landmark between said first and second dental images.

19. A computer readable storage medium as in claim 17, comprising instructions for implementing the further steps of quantifying movement, change or loss of bone between said first and second dental images in absolute units or as a relative change there between.

20. A computer readable storage medium as in claim 17, wherein said presenting step comprises the step of marking an area of interest on the first dental image and applying said formulae to identify the location of the area of interest on the second dental image.

21. A computer readable storage medium as in claim 17, comprising instructions for implementing the further steps of quantifying movement or loss of bone between said first and second dental images in absolute units or as a relative change there between.

22. A computer readable storage medium as in claim 17, comprising instructions for implementing the further steps of selecting a third dental image taken at a third point in time and repeating said adjusting and identifying steps for said third dental image with respect to said first and/or second dental images so as to document increments of change amongst said first, second and third dental images over said first, second and third points in time.

23. A computer readable storage medium as in claim 17, comprising instructions for isolating areas of two images that have moved relative to each other, aligning these areas in the two images independently, and reassembling the areas with the aligned areas repositioned in one or both images to facilitate presentation in the alternating views.

24. A computer readable storage medium as in claim 17, comprising instructions for selecting an area of one or both images upon which to base the adjustment and using only these areas to generate an adjustment that is applied to both images.

<p align="center">* * * * *</p>